United States Patent
Yoo

(10) Patent No.: US 7,336,982 B2
(45) Date of Patent: Feb. 26, 2008

(54) PHOTOPLETHYSMOGRAPHY (PPG) DEVICE AND THE METHOD THEREOF

(76) Inventor: Sun Kook Yoo, Room. 411 Hyundai zoo snag bok hab BD, (Hyundai Res. Complex BD), 48-5 Bangi-s-dong, Song pa-gu, Seoul (KR) 138-828

( * ) Notice: Subject to any disclaimer, the term of this patent is extended or adjusted under 35 U.S.C. 154(b) by 544 days.

(21) Appl. No.: 10/884,957

(22) Filed: Jul. 7, 2004

(65) Prior Publication Data

US 2005/0058456 A1    Mar. 17, 2005

(30) Foreign Application Priority Data

Jul. 7, 2003    (KR) .................. 10-2003-0045673

(51) Int. Cl.
    *A61B 5/00*    (2006.01)
(52) U.S. Cl. ...................... 600/323; 600/500
(58) Field of Classification Search ................ 600/323, 600/500
    See application file for complete search history.

(56) References Cited

U.S. PATENT DOCUMENTS

| 4,800,495 A | * | 1/1989 | Smith ............................ 600/322 |
| 5,553,615 A | * | 9/1996 | Carim et al. ................. 600/324 |
| 6,083,172 A | * | 7/2000 | Baker et al. ................. 600/500 |
| 2002/0136328 A1 | * | 9/2002 | Shimizu ..................... 375/316 |
| 2003/0036685 A1 | * | 2/2003 | Goodman ................... 600/300 |
| 2003/0225337 A1 | * | 12/2003 | Scharf et al. ............... 600/508 |
| 2004/0267140 A1 | * | 12/2004 | Ito et al. ..................... 600/500 |
| 2006/0211930 A1 | * | 9/2006 | Scharf et al. ............... 600/336 |

* cited by examiner

*Primary Examiner*—Charles A. Marmor, II
*Assistant Examiner*—Karen E. Toth
(74) *Attorney, Agent, or Firm*—Fish & Richardson P.C.

(57) ABSTRACT

A method of measuring Photoplethysmography (PPG) signals may comprise detecting dual wavelength illumination from a light detector so as to provide detected signals, converting the detected signals into digital signals so as to provide digital signals, reducing noises from the digital signals and increasing independency between the digital signals so as to provide preprocessed signals, subtracting the average value from the preprocessed signals so as to provide adjusted signals, obtaining whitening matrix based on covariance, eigen value, and eigen matrix obtained from the adjusted signals, and restoring data using the whitening matrix.

3 Claims, 7 Drawing Sheets

PHOTOPLETHYSMOGRAPHY (PPG) DEVICE AND THE METHOD THEREOF

BACKGROUND OF THE INVENTION

The present invention relates to a Photoplethysmography (PPG) device and the method thereof. More particularly, the present technology relates to a pulse oximeter device and the method measuring accurate Photoplethysmography(PPG) signals, reducing the artifacts occurred by the patient motion.

Photoplethysmography (PPG) is an electro-optic technique to measure the pulse wave of vessels.

The measuring apparatus for PPG is the pulse oximeter, which considers the relative absorption of Hemoglobin and Oxyhemoglobin to non-invasive measure of arterial oxygen saturation($SpO_2$) using the dual-wavelength illumination (LED), and the signal measured by PPG is called photoplethysmographic signal.

The arterial oxygen saturation ($SpO_2$) from PPG is a fundamental parameter to diagnose the heart and lung function, the information on the idiosyncrasy in circulating system, the status of heart vessels, and hypoxia, etc. Especially, PPG signal is one of vital signs, basic signal to measure vital parameters of a case, and therefore PPG is used as an important monitoring aid at casual wards and intensive care units.

The major factors limiting the accuracy and the general applicability in practical pulse oximetry, is low perfusion states or artifact.

The artifacts added to the oximeter limit the accuracy of measured PPG signals, are mainly occurred by the patient motion and ambient artifact, causing artifact corruption. The ambient artifact is occurred by injected environmental lights.

The ambient artifact, can be regarded to be less serious, can be appropriately removed through subtraction process, to adopt multiplexing technique against the ambient signals measured independently to restore PPG signal.

But, the motion artifact, caused by changes in optical probe coupling, patient anatomy, and optical properties of tissue due to geometric realignment, and complex combinations of all these effects, considerably deteriorates the shape of PPG signals and the value of $SpO_2$.

Moreover, the difficulty to reduce motion artifact can be aroused from that PPG and motion artifact signals mostly occupy the frequency band and time domain, same to original signal. Hence, the motion artifact reduction has been regarded as one of important issues to be handled for accurate clinical measurement.

Some methods have been researched to remove the motion artifact from PPG signals. These methods are the modeling method and three-wavelength method. Typically, the motion artifact detection method identifies the motion artifact from time sequenced PPG signals for efficient artifact concealment; and the modeling method imitates physical process of probe coupling to remove the motion artifact by the inversion of modeled artifact; and three-wavelength method subtracts the motion artifact by use of additional wavelength comparing with dual wavelengths generally used in PPG device. However, these conventional methods still contains limitation in performance for some specific noise, or limitation in mathematical modeling.

As further invention is still required to improve the performance of motion artifact rejection without adoption of fake concealment under dual wavelengths constraint, in this invention, the motion artifact reduction method under the constraint of dual wavelengths measurement was newly invented from two simplified observations.

The signal analysis to reduce motion artifact, basically utilizes independent component analysis(ICA). The basic motivation of ICA is assuming that original PPG signal is from heart pulsation, and motion artifact is another physical factor. Under the assumption, it is clearly possible to model the PPG signal measured with artifact into independent components, original PPG signal and the motion artifact. Based upon the model, the original PPG signal and the motion artifact can be separated through ICA, adopting subtraction technique to minimize the influence of ambient light. But, the practical factors causing motion artifact, also influences on the measured PPG signal, questions are raised in the given assumption, and can be recognized to have difficulties in restoring the original PPG signal by ICA technique.

Hence, the present invention discloses a new Photoplethysmography(PPG) device and the method therefor, to extract purely original PPG signal reducing motion artifact effectively to enhance the performance of conventional ICA method, combining various preprocessing techniques.

The present invention also discloses a new processing technique to reduce/eliminate motion artifact in measured PPG signal. For that; before to analyze independent components, from the periodicity of PPG signal, the period of PPG signal is extracted by using auto-correlation function; rearranges signal according to the extracted period by interleaving process; eliminates noise by time low-pass filtering; and increase the independence between PPG signal and motion artifact by innovation processing.

SUMMARY OF THE INVENTION

The present invention guarantees excellent performance in reducing motion artifact, and more of precise measuring is possible even under the motion artifact.

The present invention disclosed the method to measure $SpO_2$ by the newly proposed computing method, adopting mixing matrix in ICA, and the present invention enabled effective separation of signals by; calculating the period using auto-correlation; performing the interleaving over the period; softening the deteriorated signal through low pass filtering; increasing the statistical independence between two components; and fast ICA algorithm. Therefore, the present invention guarantees excellent performance in reducing motion artifact compared to conventional PPG measuring equipment, and more of precise measuring is possible even under the motion artifact.

The major characteristics of the present invention, is as follows.

To reduce the artifacts occurred by the patient motion and ambient noise in a pulse oximeter device for accurate Photoplethysmography(PPG) signals, the present method discloses following steps; a light detecting step to detect dual wavelength illumination from a light detector; A/D conversion step, converting the said detected analog signals into digital ones; preprocessing step reducing noises from the each of outputs from the said A/D conversion step, and to increase independence between the signals; centering process step to subtract the average value from the said outputs of preprocessing step; whitening process step to drive out whitening matrix, by calculating covariance, it's eigen value and eigen matrix from the outputs of the said centering process step; data restoring step to restore data from the output of whitening process setp.

The present method to measure Photoplethysmography (PPG) signals discloses following steps; a light detecting step to detect dual wavelength illumination from a light detector; A/D conversion step, converting the said detected analog signals into digital ones; preprocessing step reducing noises from the each of outputs from the said A/D conversion step, and to increase independence between the signals; centering process step to subtract the average value from the said outputs of preprocessing step; whitening process step to drive out whitening matrix, by calculating covariance, it's eigen value and eigen matrix from the outputs of the said centering process step; calculating step for the matrix W, to calculate out a demixing matrix W, repeatedly adopting the contrast Gaussian function; calculating step for a mixing matrix A, to calculate out using the outputs from the said whitening process step and the said calculating step for the matrix W; data restoring step to restore data using the said calculating step for the matrix W and the said calculating step for the matrix A.

The said preprocessing step also discloses following steps in detail; period measuring step to drive out the period of Photoplethysmography(PPG) signals, output from the said A/D conversion step, using autocorrelation; interleaving process step, to relocate data in a given sequence of amplitude according to the said calculated period; time low-pass filtering step to transform over the all sampling points into the average value of current point, previous point, and next point; the innovation process step to subtract the average up to the previous value, from current output of the said time low-pass filtering step.

The said data restoring step discloses following steps in detail; a step to decide PPG signal between separated PPG signal and noise signal using demixing matrix W, and then restoring the sign and gain of measured PPG signal using the mixing matrix A; calculating step to calculate the ratio R of the normalized transmitted amount of red and infrared lights, from the said matrix A; the step calculating the arterial oxygen saturation ($SpO_2$), using the said R, by the given formula.

arterial oxygen saturation $(SpO_2)(\%) = a - bR$, (where, $107 \leq a \leq 110, 25 \leq b \leq 32$)

The present Photoplethysmography(PPG) measuring device comprises; the light emitting unit composed of two LEDs(light emitting diodes) to emit dual beams of different wavelengths, and a driving circuit for said LEDs; the light detector unit to transform the said transmitted or reflected lights of dual wave lengths, into electrical signals; input separating circuit to amplify the output from the said the light detector unit, and to reduce ambient artifact; A/D converter unit to convert the output analog signals from the said input separating circuit, into digital signals; digital signal processing unit to reduce motion artifact from the output of the said A/D converter unit; a computer unit to evaluate, store, and display the received output signal from the said digital signal processing unit.

The communication between the said digital signal processing unit and the said computer unit, to transmit the output from the said digital signal processing unit to the said computer unit, is performed in wire and/or wireless channel.

DETAILED DESCRIPTION OF THE DRAWINGS

The above objects and the other features of the present invention will become more apparent by describing in detail preferred embodiments thereof with reference to the attached drawings, in which.

DETAILED DESCRIPTION OF THE INVENTION

Hereinafter, the present invention on a Photoplethysmography (PPG) device and the method thereof, are described in detail with reference to its theoretical background and the accompanying drawings.

First of all, the characteristics of PPG signal can be described as follows.

The mechanism used to measure PPG signal by a pulse oximeter, is that heart pulsation causes changes in absorption coefficients of hemoglobin and oxyhemoglobin in wavelength function. Especially, absorption characteristics of hemoglobin and oxyhemoglobin are changed near the wavelength of red light(660 nm) and near infrared(890 nm) region, it is possible to measure PPG signal using those two lights of different wavelengths.

Figure 1:
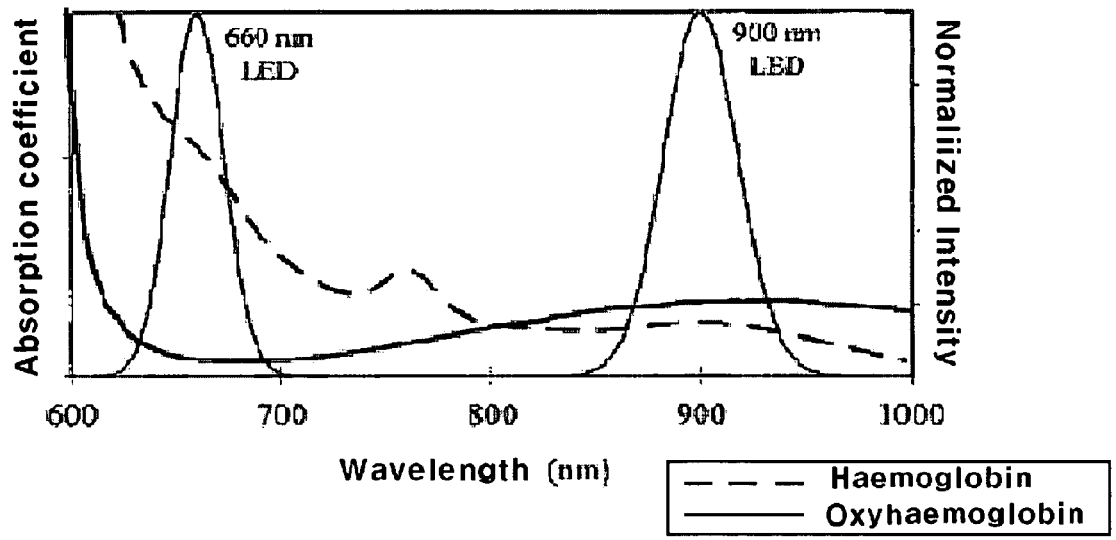
FIG. 1 is a graph for the normal wavelength distribution of each LED, with absorption coefficient according to the wavelength.

FIG. 1 is a graph for the normal wavelength distribution of each LED, with absorption coefficient according to the wavelength, the solid line is for hemoglobin and the dotted line is for oxyhaemoglobin, respectively.

Also, $SpO_2$ is given as following formula (1).

$$SpO2\ (\%) = \frac{[O_2Hb]}{[O_2Hb] + [Hb]} \times 100 \qquad (1)$$

$SpO_2$ means the percentage of oxyhaemoglobin to the total sum of hemoglobin and oxyhemoglobin in blood, in case of normally healthy person, it closes to the value of 100.

In conventional method, the value of $SpO_2$ at the practical diagnosis, can be calculated using weighted moving average (WMA) method. This method enables time domain signal processing, within $\pm 2\% (\pm 1$ of variance) of error.

Recently developed algorithm to enhance the measured $SpO_2$, also uses Fast Fourier Transform(FFT) and Discrete Cosine Transform(DCT). Applying the said algorithm with the sampling rate of 15 Hz and 64 point FFT, $SpO_2$ can be calculated by the formula (2).

$$SpO_2\ (\%) = 110 - 25 \times R \qquad (2)$$

The R is the normalized ratio between the amount of transmitted red and infrared lights. And also, the R can be expressed as the following formula (3).

$$R = \frac{AC_R/DC_R}{AC_{IR}/DC_{IR}} \quad (3)$$

$AC_R$ component is signal variation in transmitted red light, and $AC_{IR}$ component is signal variation in transmitted infrared light, followed by heart pulsation. $DC_R$ component is the total average of transmitted red light, and $DC_{IR}$ component is the total average of transmitted infrared light. AC components, $AC_R$, $AC_{IR}$ are expressed in peak-to-peak value of output signals.

However, when motion artifact is injected into signal to vary output AC value in a considerable amount, it is impossible to measure $SpO_2$ precisely.

Hence, the present invention offers a technique to measure the values R and $SpO_2$, after restoring original PPG signal through the proposed real-time motion artifact reducing system.

Next, principle component analysis(PCA) adopted to the present invention will be described.

The principle component analysis(PCA) is a method widely used in the fields of signal processing, statistics, neural computing, and sometimes called as "Karhunen-Loeve transform"(KLT). The basic concept of the principle component analysis(PCA) is, to find out the concerned components among linearly transformed components of the number n, using the maximum value of possible variance. This is defined as an intuitive method through some repeated calculations.

In the first step of principle component analysis(PCA), vector x is centered by subtracting it's average value(ie. $x \rightarrow x - E\{x\}$). Then, transformed into another vector y with m elements, to decrease overlapping in correlation. This process is to find out circulated orthonormal coordinate system, to let x uncorrelated in the new coordinate system. At the same time, the variance of projected vector x can be maximized on the new coordinate, so the first axis can be laid in the direction of maximum variance, while the second axis is to the perpendicular to the first axis.

It can be written in the following formula (4), letting $w_1$ the direction of the first principle component $y_1$.

$$y_1 = \sum_{k=1}^{n} w_{k1} x_k = w_1^T x \quad (4)$$

$$w_1 = E\{y_1^2\} = \arg\max_{\|w\|=1} E\{(w^T x)^2\} = w_1^T E\{xx^T\} w_1 = w_1^T C_x w_1$$

where, $w_{11}, \ldots, w_{n1}$ are the weights of nth dimensional vector $w_1$, and $w_1$ is of mth dimension same as data vector x. Therefore, the first principle component can be projected toward the maximum projection direction. When k-1th principle component is decided, kth component is expressed by the difference in previous value as the formula (5).

$$w_k = \arg\max_{\|w\|=1} E\left\{\left[w^T\left(x - \sum_{i=1}^{k-1} w_i w_i^T x\right)\right]^2\right\} \quad (5)$$

The principle component given by $y_i = w_i^T x$, is calculated by covariance matrix $C = E\{xx^T\}$. When order eigenvalue $d_1, \ldots d_n (d_1 \geq d_2 \geq \ldots \geq d_n)$, corresponding to eigenvector per unit length of C, $e_1, \ldots e_n$, it results in $e_i = w_i$.

PCA (principle component analysis) is an optimal linear dimension reduction technique, using mean-square. It enables compression to decrease overlapping in x, using cross-correlation between given elements. This dimension reduction technique can have some of important merits. First, it offers convenience in computing, to decrease overhead in a processing stage. Second, it reduces the influence of noise. Third, it is useful to predict data, for to be projected into a subspace of very low dimension. It is important that there is no need to use n of principle components.

In a subspace, some of other orthonormal basis effects on data compression or noise reduction, in conjunction with principle components.

The purpose of PCA (principle component analysis) is concerned with the purpose of ICA (independent component analysis).

But, the property of overlapping can not be emphasized in ICA, when the overlapping is measured by correlation between data components in PCA with increased independence. PCA becomes useful preprocessing step in ICA, for it eliminates cross correlation, and decreases the effect of first and second-order statistics through centering and whitening.

Next, the ICA process will explained. A brief summary of the ICA process will be provided first and a more detailed explanation will follow. Signals mixed with noise, which were obtained by n sensors at time t, may be represented by $x(t) = [x_1(t) \ldots x_n(t)]^T$. This x(t) satisfies the equation $x(t) = A \cdot s(t)$, where x(t) are the mixed signals from the sensors, s(t) are original signals without noise, and A is an arbitrary mixing matrix (N×M scalar matrix). The ICA process is used to find out the demixing filter W for demixing the original signals from the mixed signals. The demixing filter output may be represented by the equation $y(t) = Wx(t)$, where y(t) are demixed signals whose volume and order are changed from the original signals. W is called a demixing matrix. W may be obtained by applying non-linear functions using, for example, a fix-point algorithm. Then, A, the inverse matrix of W, may be obtained, and data may be restored using the A matrix and original data x(t). The ICA process is explained in further detail below.

To define ICA, a statistical "latent variables model" will be utilized. The measured output for n of components is a linear combination of the multiplication of each component and mixing matrix (see formula (6)).

$$x_j = a_{j1} s_1 + a_{j2} s_2 + \cdots + a_{jn} s_n, \text{ for all } j \quad (6)$$

This establishes under the assumption that n of components should be statistically independent with Gaussian distribution, and unknown mixing matrix is in square form. If non-Gaussianity is not guaranteed for inputs, it would cause slow processing time for estimation.

The mechanism of ICA estimation is based upon Central Limit Theorem, that the distributed sum of independent random variable is more gaussian. Assuming all the components have identical distribution, it can be expressed as formula (7).

$$y = w^T x = \Sigma_i w_i x_i \text{ (where, w is determined vector)} \quad (7)$$

Then, w is one of columns in inverse matrix of A, and for estimation, z can be newly defined as formula (8).

$$Z = A^T w \rightarrow y = w^T x = w^T A s = z^T s \quad (8)$$

$z^Ts$ becomes same to the one of $s_i$, when $z^Ts$ gets more gaussian than any other one of $s_j$, then the vector w to maximize nongaussianity of $w^Tx$ should be found out. It is known as objective(contrast) function to maximize or minimize some property for estimation.

Next is the explanation on the Fast ICA algorithm.

The basic method to maximize contrast function, is the adaptive algorithm based on stochastic gradient descent. It is fast adaptive even under the nonstationary circumstance. But the speed of convergence is relatively slow, and considerably influenced by learning rate selection. Besides, the fixed-point algorithm of recent interest, which is known Fast ICA, has fast convergence speed and unique characteristic, because it calculates large data in one step at a time.

Another characteristic of fixed point algorithm is to find out directly an independent component with non-Gaussian distribution, using a certain non-linearity function g.

Hence, the performance of the method can be optimized, by choosing proper g of non-linearity, then each of independent components is estimated one by one as done in the projection pursuit. To pursuit an independent component, firstly the maxima of Negative Entropy(Negentropy) is found from the optima of E $\{G(w^Tx)\}$. Under Kuhn-Tucker condition within the range of $E(w^Tx)2=|w|2=1$, the optima of $E\{G(w^Tx)\}$ is decided as a point given in formula (9).

$$E\{xg(w^Tx)\}-\beta w=0 \quad (9)$$

where, $\beta=E\{w_0^T xg(w_0^T x)\}$, and $w_0$ is the optimum value of w.

Solving this by Newton's method, it results in a Jacobean matrix JF(w), as shown in formula (10).

$$JF(w)=E\{xx^T g'(w^Tx)\}-\beta I \quad (10)$$

To make inversion of the matrix simple, JF(w) becomes diagonal by approximation of the first term, and approximate Newton iteration can be done by approximating $\beta$ using present value of w, instead of $w_0$.

$$w^+=w-[E\{xg(w^Tx)\}-\beta w]/[E\{g'(w^Tx)\}-\beta]$$

$$w^*=w^+/\|w^+\| \quad (11)$$

$w^*$ is new value of w, and $\beta=E\{w^T xg(w^Tx)\}$.

Dividing the both side of formula (11) with $\beta-E\{g'(w^Tx)\}$ to simplify, it becomes fixed-point algorithm expression (see formula (12)).

$$w^+=E\{xg(w^Tx)\}-E\{g'(w^Tx)\}w$$

$$w^*=w^+/\|w^+\| \quad (12)$$

As mentioned above, to pursuit n components by one unit estimation, it should be repeated by n times. By adding orthogonalizing projection into the loop, estimating different independent component is also possible for each time. Projecting present w(k) over orthogonal space formed by the column of mixing matrix B, one each of independent components can be found out at a time. Letting B' the previous value of column in B, it is as given in formula (13).

$$w(k)=w(k)-B'B'^T w(k) \quad (13)$$

Here, divide w(k) with it's norm.

This additional projection is performed prior to start iteration and to perform the estimation.

Next is the explanation on additive algorithm in preprocessing.

It still has difficulties in perfect restoration, to adopt ICA algorithm to practical data. Hence, the present invention proposes additive algorithm in preprocessing, to overcome the problems arisen from the fact, that measured PPG signal is mainly influenced by noise, and the signal from given dual channels are almost similar.

The additive algorithm proposed in the present invention contains; period measurement using autocorrelation, interleaving process, time low pass filtering, innovation process.

Firstly, period measurement using autocorrelation is described in the followings.

The original PPG signal has periodical characteristics, according to heart pulsation. Even for the periodical characteristics deteriorated by motion artifact, it is possible to extract period data, adopting autocorrelation over a given interval of the signal.

The auto-correlation $\beta(k)$ of the measured signal is expressed as formula (14):

$$\phi(k) = \lim_{N \to \infty} \frac{1}{(2N+1)} \sum_{m=-N}^{N} x(m)x(m+K) \quad (14)$$

Formula (15) is for a signal with period P.

$$\phi(k)=\phi(k+P) \quad (15)$$

From this paragraph, the explanation on interleaving process in the present invention is followed. Interleaving process is the method, generally applied to mobile communication, of relocation used to reduce burst error in transmitted bit stream. For example, when 5 of 7 bit Hamming code words were expressed as follows;

1234567 1234567 1234567 1234567 1234567

The signal output through interleaver, is as follows.

11111 22222 33333 44444 55555 66666 77777

Then it becomes possible to detect and correct the signal from burst error, by relocating received signal.

Adopting this mechanism to PPG, is rearranging the signal according to the period extracted from autocorrelation process.

The following paragraph is describing on the time low pass filtering process.

Any of linear filtering can be used to the signal in time series, and it doesn't change the given ICA model. When the relation between observed signal and original signal can be expressed as; X=AS, and defining the time filtering matrix M, it also establishes the relation; X*=XM=ASM=AS*. This shows it still contains ICA model, and the filtering over independent component is also applied to mixtures. Low pass filtering is changing each sample points into the average value of the selected point, previous point, and next point. It is performed in the form of smoothing, and can be expressed by the matrix M of formula (16).

$$M = \frac{1}{3} \begin{bmatrix} & & & \vdots & & & & \\ \cdots & 1 & 1 & 1 & 0 & 0 & 0 & 0 & 0 & \cdots \\ \cdots & 0 & 1 & 1 & 1 & 0 & 0 & 0 & 0 & \cdots \\ \cdots & 0 & 0 & 1 & 1 & 1 & 0 & 0 & 0 & \cdots \\ \cdots & 0 & 0 & 0 & 1 & 1 & 1 & 0 & 0 & \cdots \\ \cdots & 0 & 0 & 0 & 0 & 1 & 1 & 1 & 0 & \cdots \\ \cdots & 0 & 0 & 0 & 0 & 0 & 1 & 1 & 1 & \cdots \\ & & & \vdots & & & & \end{bmatrix} \quad (16)$$

Since the measured PPG signal and motion artifact noise occupies same frequency band, it is impossible to reduce motion artifact effectively by conventional frequency filtering methods. But, block interleaving rearranges periodic sample points into low frequency component, while it rearranges non-periodic sample points into high frequency component. Because of this frequency rearrangement property of the interleaving, the high frequency components (noises) are removed by the time low-pass filtering without deteriorating PPG signal, even though the PPG and noises occupied the same frequency band.

In the following paragraph, the innovation process will be explained.

For a given stochastic process s(t), the innovation process $\tilde{s}(t)$ can be defined as the error in best prediction process. As the best prediction method is the expectation value of conditional distribution to s(t), it can be driven out by the conditional expectation of previous value. Hence, the innovation process is defined as in the formula (17).

$$\tilde{s}(t)=s(t)-E\{s(t)|s(t-1),s(t-2),\}\quad(17)$$

The innovation process guarantees the result more independence and more Gaussian than original process. This is because the process is based on Central Limit Theorem, that $s_i(t)$ is a kind of moving average, and that the distributed sum of independent random variable is more Gaussian.

From the following, the composition and operation of Photoplethysmography of the present invention will be explained as an example according to the figures attached.

Figure 2:
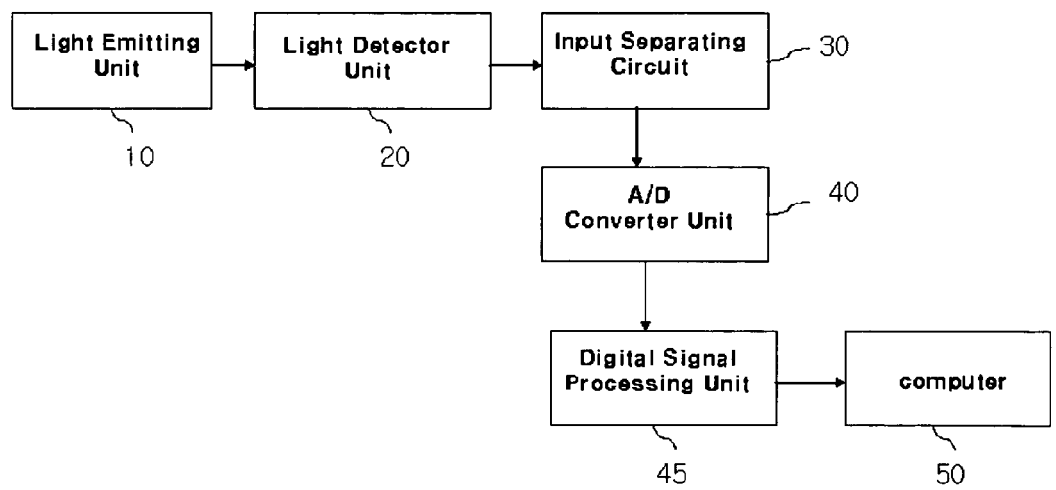
FIG. 2 is a block diagram of the Photoplethysmography (PPG) device, according to an embodiment of the present invention.

FIG. 2 is a block diagram of the Photoplethysmography system, comprising of light emitting unit 10, light detector unit 20, input separating circuit 30, A/D converter unit 40, digital signal processing(DSP) unit 45, and computer 50.

The light emitting unit 10 composed of two LEDs(light emitting diodes) to emit dual beams of different wavelengths, and a driving circuit for said LEDs. The said LEDs can be selected both at the wave length of red light(660 nm) and near infrared light(890 nm) for light emitting unit 10. The said driving circuit for said LEDs supplies constant current to the said LEDs of dual wavelengths. At this time, current control function can be added to let the measured DC values from two channels keep constant, to compensate dynamic range and to guarantee convenience in measurement of the R.

Light detector unit 20 is to detect transmitted or reflected dual beams, then to convert into electrical signals, and can be composed of photo diodes.

Input separating circuit 30 reduces ambient artifact, after amplifying the serial input from the light detector unit 20, with the minimum gain. That is, the output from the light detector unit 20 is amplified by a differential amplifier, then separated into ambient signal and the others in different bands by analog multiplexer. The AC component of PPG can be acquired through eliminating ambient artifact, to subtract ambient signal from the other signals in different bands, and by DC filtering and AC gain control.

A/D converter unit 40 is to convert the analog signal from the said input separating circuit 30 into digital signal. For input separating circuit 30, the A/D converter of 24 bit resolution can be used. When the output from input separating circuit 30 is converted in 24 bit or higher resolution, the dynamic range reduction can be compensated. The sampling rate of A/D converter can be selected to 500 Hz.

The digital signal processing(DSP) unit 45 reduces motion artifact from the said A/D converter unit 40. Especially, the said digital signal processing(DSP) unit 45 also performs the functions of; eliminating white light, AC/DC filtering, nonlinear equalizer, measuring SpO$_2$, calculating heart pursation, gain control, reducing motion artifact.

Computer unit 50 is to evaluate, store, and display the received output signal from the said digital signal processing unit 45.

The communication between the said digital signal processing unit 45 and the said computer unit 50, to transmit the out put from the said digital signal processing unit 45 to the said computer unit 50, can be performed in wire and/or wireless transmission.

In the present invention, the algorithm developed to reduce motion artifact, basically can use ICA method, after four kind of processes; measuring the period, interleaving process, time low pass filtering, innovation process. Enhancing the performance by using the said four of combined process, and adopting ICA and PCA together, is specific algorithm proposed in the present invention. The ICA algorithm of the invention is Fast ICA one.

Figure 3:
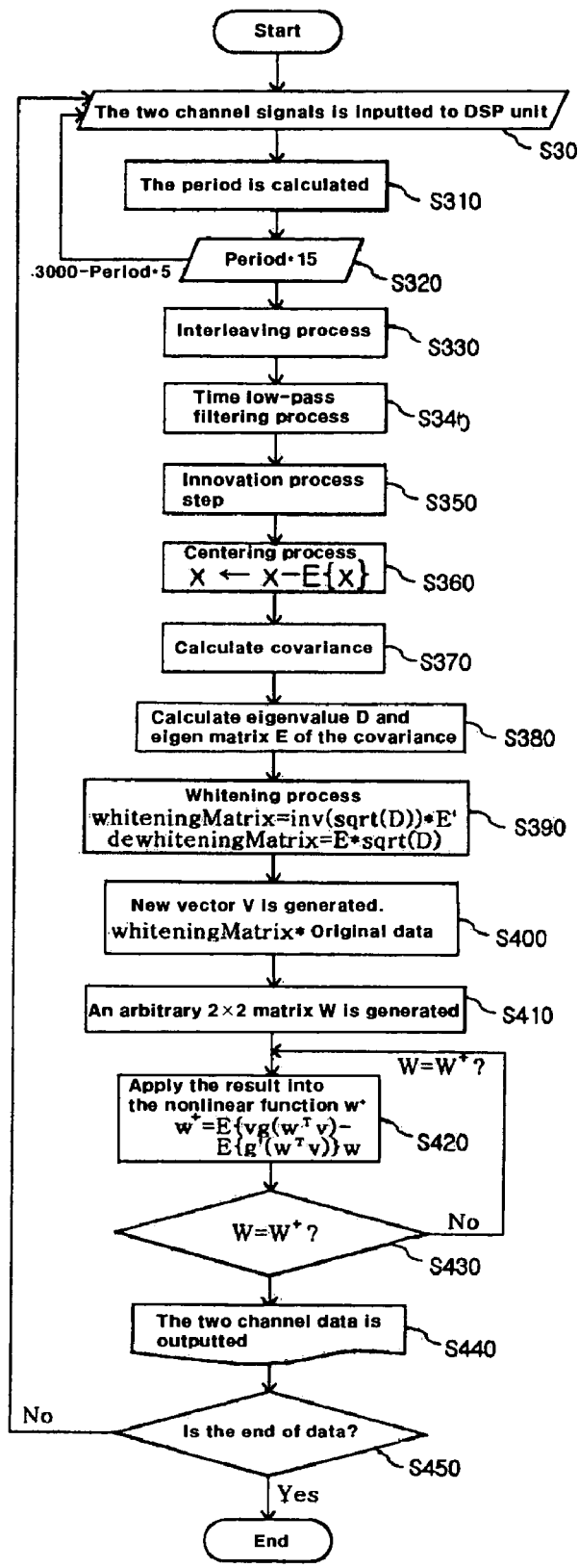
FIG. 3 is a flow chart to reduce motion artifact using independent component analysis, according to an embodiment of the present invention.

FIG. 3 is the flow chart as an example to reduce motion artifact using ICA, comprising; preprocessing step, PCA step, and ICA step. The two channel signals detected by light detector unit 20, is converted into digital data and inputted to digital signal processing(DSP) unit 45 (step S300). Then the period is calculated by computing to average distance among the maximum values in the inputted data (step S310). The example is for selecting 15 of period blocks. In this example, 15 of period blocks were selected however, this number can be chosen into any other numbers. Interleaving process can be performed over the said 15 period blocks, to rearrange in the sequence of magnitude (step S330). Then time low-pass filtering process is performed over the all sampling points to transform each point into the average value of current point, previous point, and next point (step S340). The innovation process step is followed, to subtract the average up to the previous value, from current output of the said time low-pass filtering step (step S350).

Next centering process is to subtract the average value from the signal output of the said innovation process (step S360). To calculate covariance from the output (step S370), to drive out the eigenvalue D and eigen matrix E of the covariance (step S380), then whitening process is performed using the eigenvalue D and eigen matrix E of the covariance (step S390), by calculating whitening matrix and dewhitening matrix as in the formula (18).

whiteningMatrix=inv (sqrt $(D))*E'$ dewhiteningMatrix=$E$*sqrt $(D)$ (18)

Using the said whitening matrix and the original data, a new vector V given in the form of whitening Matrix*original data is generated (step S400). From this, an arbitrary 2×2 matrix W is generated as in the formula (19) (step S410). And apply the result into the nonlinear function w$^+$(step S420).

$$w^+=w-E\{vg(w^Tv)\}-E\{g'(w^Tv)\}w\quad(19)$$

Then the two channel data, when the matrix w and the nonlinear function w$^+$is equal, can be outputted (step S430).

The whole flow chart of the present invention, according to an example, is in the following sequence.

First, the period is measured after storing the given number of data. The number of data can be chosen to be 2500.

Second, the data over 10 time of period, are used and the rest of those are returned. The present example uses the data over 10 time of period however, the number of data used is variable into a certain number.

Third, the preprocessing is performed, comprising of; interleaving process, time low pass filtering, innovation process.

Forth, centering process is performed.

Fifth, after calculating covariance with it's eigenvalue and eigen matrix, whitening is performed.

Sixth, using the repeating contrast Gaussian function, the demixing matrix W is calculated. When it is repeated over the maximum repeating times, it is terminated and the result is substituted by the previous output.

Seventh, using the said fifth and sixth results, mixing matrix A is calculated.

Eighth, using the said matrix A and W, restore the original signal, compute R, and calculate $SpO_2$. At this process, the result of ICA can be outputted.

This eighth step is to decide PPG signal between separated PPG signal and noise signal using demixing matrix W; and then restoring the sign and gain of measured PPG signal using the mixing matrix A; calculating step to calculate the ratio R of the normalized transmitted amount of red and infrared lights, from the said matrix A; the step calculating the arterial oxygen saturation ($SpO_2$), using the said R, by the given formula (21).

Finally, the process is repeated from the first step, until the end of data.

Figure 4:
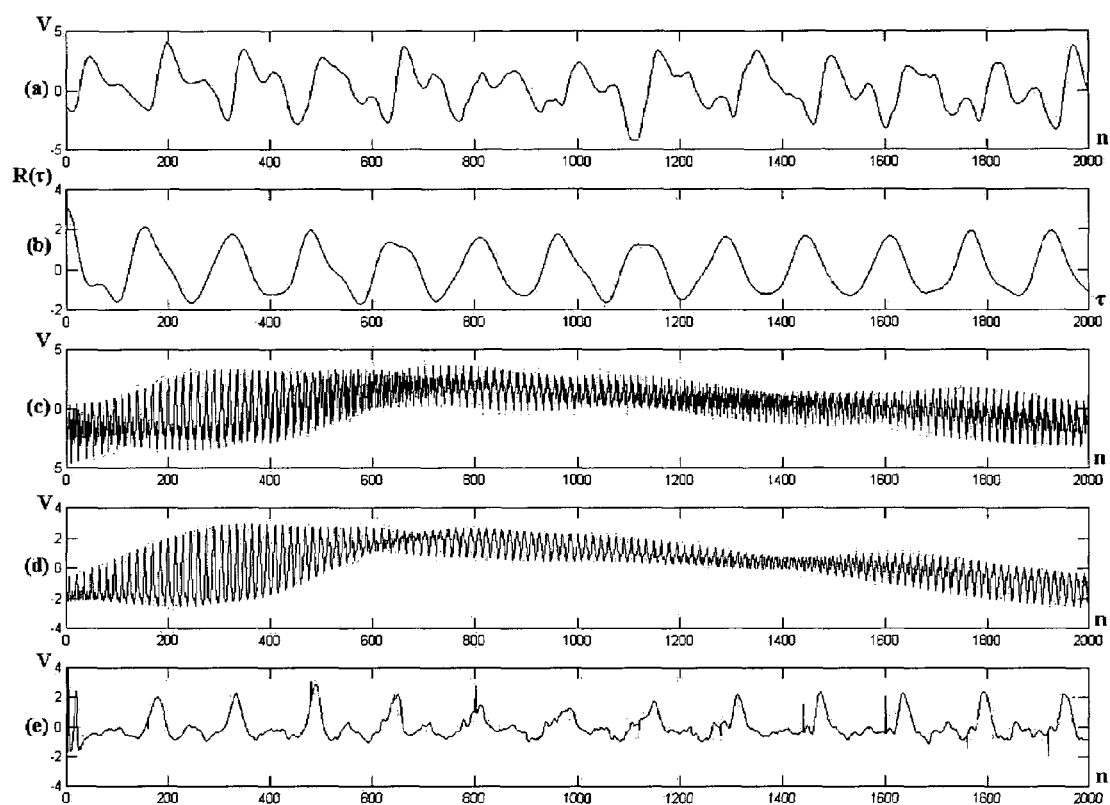
FIG. 4 is an example of PPG signal interleaved from original signal and measured one with motion artifact.

FIG. 4 shows a given example of the result from interleaving process upon a measured PPG including motion artifact. FIG. 4(b) is auto-correlation of the measured PPG including motion artifact in FIG. 4(a). It is maximum at the very beginning, and has other maximum values with a regular interval. Therefor, the average of the maximum values over the threshold can be decided as period. Even though the signal is severely deteriorated due to the motion artifact injected over some interval, it can't influence the period measurement, because the data used for auto-correlation are over than 10 periods. FIG. 4(d) is the wave data before adopting time low pass filtering. The signal gets clearer than FIG. 4(c), which is the result of interleaving only, before the filtering. FIG. 4(e) is the result of innovation process for the time low pass filtered output, after restoring the original signal through re-interleaving. The spikes in FIG. 4(e) are interleaving error, and those can be separated as artifact component in ICA.

Next, the experimental result of the present invention compared to the conventional PPG measuring equipment and method, will be explained. The experiment was performed for the case of bending motion with small vibration in the up-down direction over a fixed wrist, and the case of random motion as artifact, respectively. The results are shown in the FIG. 5 to FIG. 8.

Figure 5:
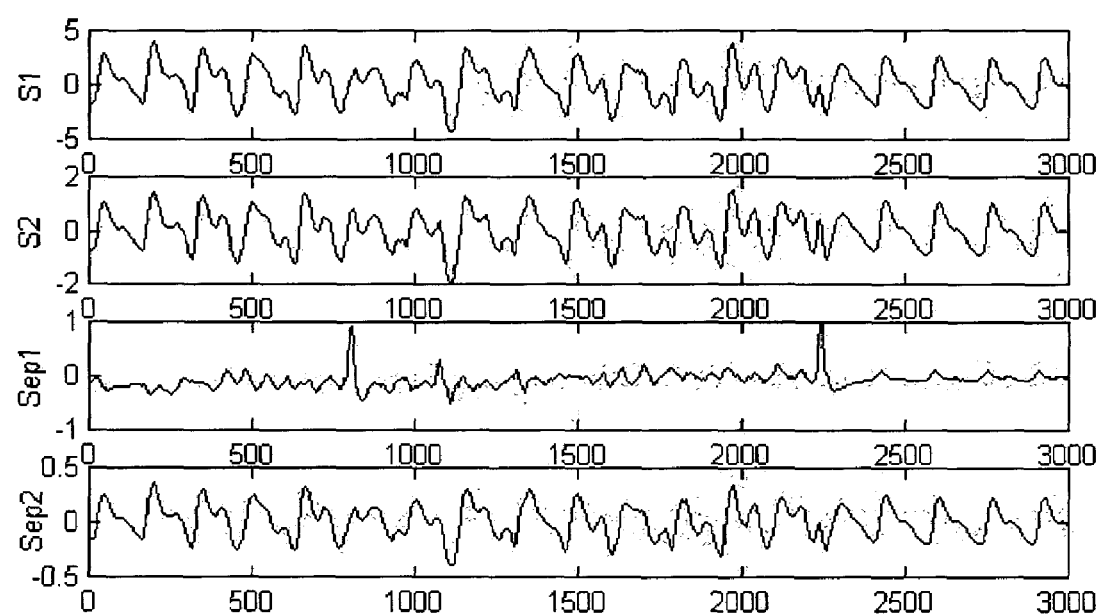
FIG. 5 is an example of the result of separated PPG and motion artifact, adopting only conventional independent component analysis(ICA)

FIG. 5 is a given example of the result adopting the conventional ICA method only. In the figure, s1 is observed infrared(IR) light signal and s2 is for red light signal, and Sep1 and Sep2 is the separated signals according to wavelengths through ICA.

As shown in the FIG. 5, motion artifact and original PPG can not be separated clearly by the basic ICA method, on the contrary, it shows to be separated into PPG with artifact (FIG. 5(d)) and small level noise(FIG. 5(c)). These result proves that the original signal and motion artifact can be hardly separated, because of the correlation between the two signals.

Figure 6:
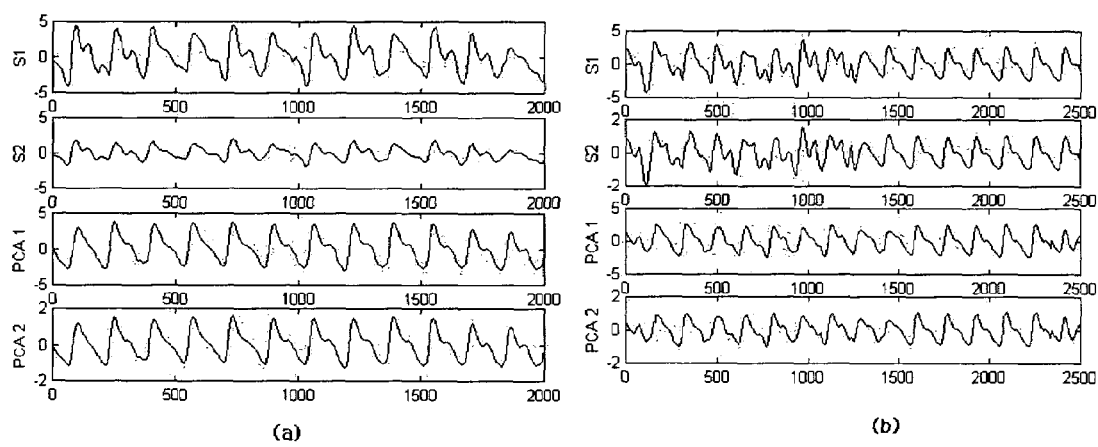
FIG. 6 is an example of the result of separated PPG and motion artifact, adopting principle component analysis (PCA) with preprocessing procedures, according to an embodiment of the present invention.

FIG. 6 is an example of result separated through PCA including the preprocessing steps of the present invention. FIG. 6 is the result of PCA including the preprocessing steps of the present invention for the PPG with motion artifact, and s1 is infrared(IR) light signal and s2 is red light signal of given wavelengths, and PCA1 and PCA2 are the results taken through PCA.

FIG. 6(a) is for bending motion, and shows smoothed motion artifact. FIG. 6(b) is the case of random motion for 3 seconds as artifact, and shows PCA output is restored almost without deterioration.

Figure 7:
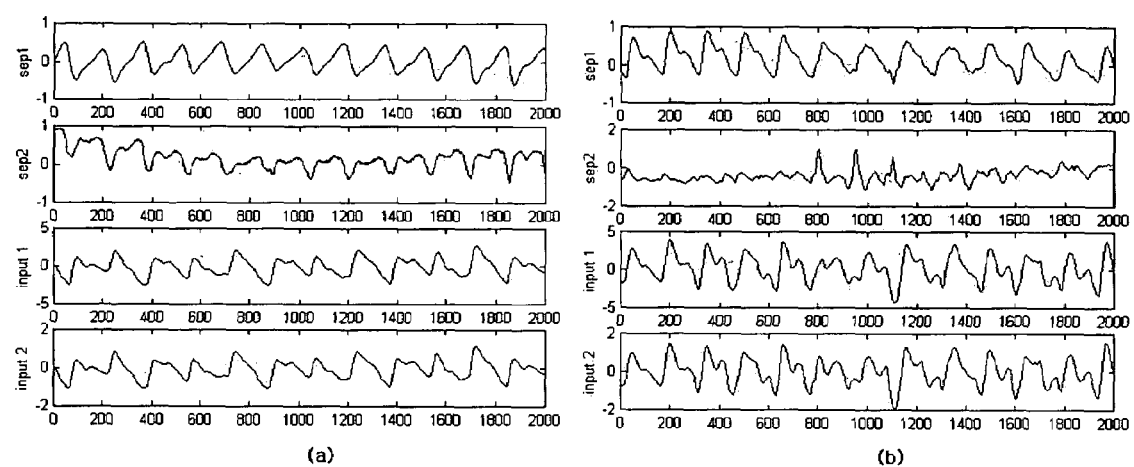
FIG. 7 is an example of the result of separated PPG and motion artifact, adopting step up to independent component analysis, according to an embodiment of the present invention.

FIG. 7 is a given example of the invention, the result processed to ICA, that is processed through preprocessing, PCA, and ICA. In FIG. 7, input1 is the observed infrared(IR) light signal, input2 is the observed red light signal, sep1 is original signal, and sep3 is separated noise signal. The waveform in FIG. 7 was taken through; preprocessing step comprising period measuring, time low pass filtering, innovation process; PCA; then primary components were separated one by one through repeated Gaussian nonlinear function. It shows that the signal level gets constant to a certain level, and the input is separated into PPG and motion artifact when input has no saturation.

But, looking over the separated signals through ICA as in FIG. 7, the waveform is restored only, while the gain and sign are not. As long as, PPG is an important factor not only to calculate the shape of AC component, but also to compute $SpO_2$, the present invention proposes a formula to compute $SpO_2$ using ICA.

In ICA model, the observed two variables can be expressed as in the formula (20).

$$\begin{bmatrix} x_1 \\ x_2 \end{bmatrix} = \begin{bmatrix} a_1 & a_2 \\ b_1 & b_2 \end{bmatrix} \begin{bmatrix} s_1 \\ s_2 \end{bmatrix} \quad (20)$$

When, letting X be the output with motion artifact, $s_1$ becomes original PPG, and $S_2$ can be assumed to be motion artifact. Without motion, $S_2$ is separated as random noise. Then $a_1$ contains the information of original signal for IR wavelength, $a_2$ becomes motion information over IR measurement. In the same way, $b_1$ contains the information of original signal for red light wavelength, and $b_2$ becomes motion information over red light measurement. Therefore, the value of R in the present invention establishes $R=b_1/a_1$. As for this value, only the AC part for gain control without the influence of DC component, was considered, the result is in a little bit decreased value. By the repeating experiment for the conventional formula to calculate $SpO_2$, the formula (2) ($SpO_2(\%)=110-25\times R$), the value of R is 0.48~0.56 for normal person within the 96%~98% $SpO_2$.

Meanwhile, the value of R computed in the present invention is within the range of 0.35~0.45, and the first term of the formula (2) can be approximated as formula (21) in accordance to 96~98(%) of $SpO_2$ value. In the formula (21), varing the gradient of b makes b=(0.45−0.35)/(0.56−0.48) =1.25, then 25×b=32. For a, the relation a=25×(0.48−0.35) results 110−a=107. Hence, the new formula for computing $SpO_2$ is approximated as formula (21).

$SpO_2(\%)=a-bR$ (where, $107 \leq a \leq 110$, $25 \leq b \leq 32$) \hfill (21)

An example of formula (21) to compute $SpO_2$ is the formula (22).

$SpO_2(\%)=107-25\times R$ or, $=110-\mathbf{32}\times R$ \hfill (22)

In the formula (20), the information to be known additionally is that which one is the original PPG between $s_1$ and $S_2$. As long as the characteristics of ICA restores the shape of signal only, rather than the gain and sign, the separated signal of the first channel can be both of original signal and motion artifact.

This problem of indefiniteness is solved in the present invention, adopting demixing matrix W, given as S=WX. W can be generated from eigen vector and singular value decomposition, and can be taken through repeating projection and nonlinearlity. So the matrix w means the importance of the information. Therefore, by comparing W[1][1] and W[2][1] to output larger value, the original signal can be decided.

In conclusion, when $x_1=a_1 \times s_1 + a_2 \times s_2$, $s_1$ becomes original PPG and $s_2$ is motion artifact. Then $a_2$ can be substituted into zero, then $x_1=a_1 \times s_1$, $x_2=b_1 \times s_1$ established, so the signal can be restored.

Figure 8:
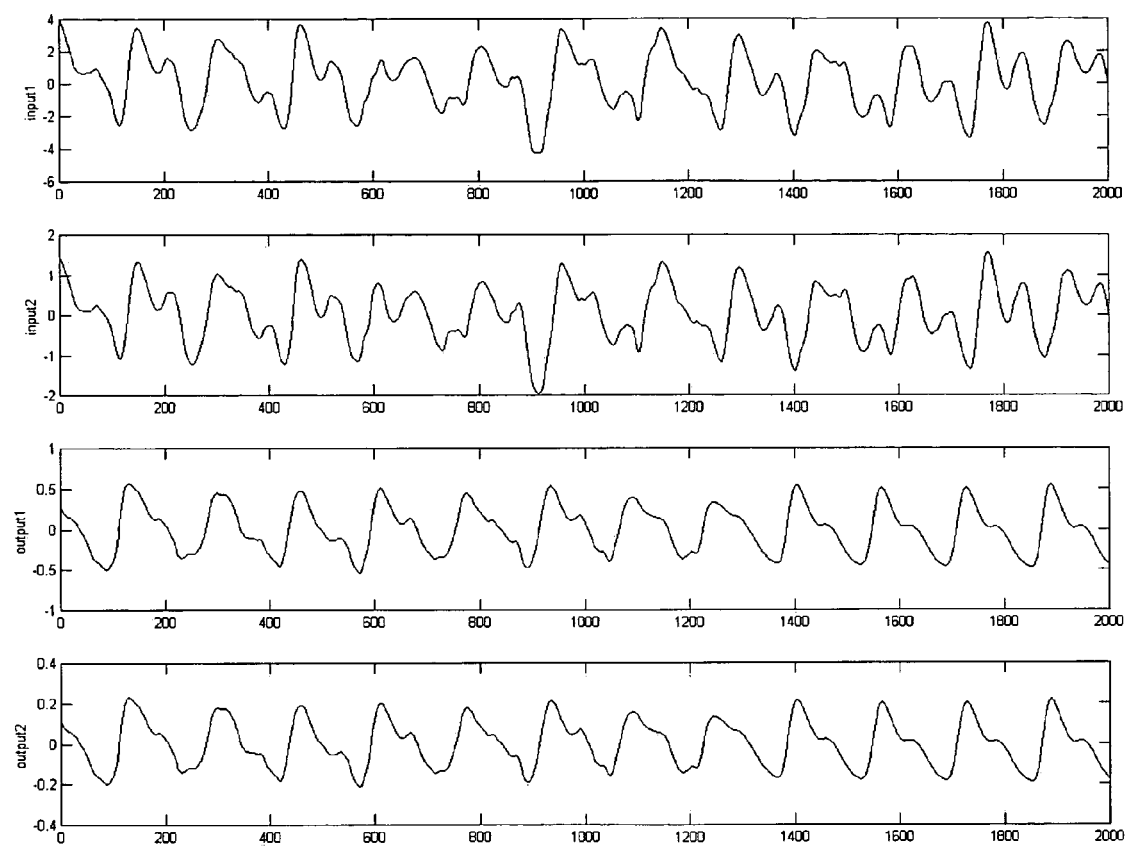
FIG. 8 is an example of restored PPG signal from the Photoplethysmography(PPG) device, according to an embodiment of the present invention.

FIG. 8 shows an example of the result measured by the $SpO_2$ measuring device of the present invention.

In the present invention, the original PPG was restored by separating the PPG and motion artifact signal from the motion added signal, by additive preprocessing step to the basic ICA algorithm. And the present invention adopted a new computational method to measure $SpO_2$ adopting mixing matrix into ICA.

Furthermore, the present invention enabled effective separation of signals by; calculating the period using autocorrelation; performing the interleaving over the period; softening the deteriorated signal through time low pass filtering; increasing the statistical independence between two components; and fast ICA algorithm.

The present invention guarantees excellent performance in reducing motion artifact compared to conventional PPG measuring equipment, and more of precise measuring is possible even under the motion artifact.

In addition, the present invention has effect to reduce motion artifact, added to PPG while the measurement performed upon the case in walking. And make it easier for the senior people to measure PPG at home, or in the field of sports medical science, the condition of the athletes can be easily and precisely measured.

In here, although the preferred embodiments of the present invention have been described, it will be understood by those skilled in the art that the present invention should not be limited to the described preferred embodiments, but various changes and modifications can be made within the sprit and scope of the present invention as defined by the appended claims.

What is claimed is:

1. A method for measuring arterial oxygen saturation ($SpO_2$), the method comprising:

in a light detecting step, detecting red and infrared lights from a light detector;

in an A/D conversion step, converting the detected signals of the light detecting step into digital signals;

in a preprocessing step, removing noises from the digital signals of the A/D conversion step and then performing an innovation process, to increase independence between a measured Photoplethysmography (PPG) signal and motion artifact noise;

in a centering process step, subtracting an average value from output signals from the preprocessing step;

in a whitening process step, obtaining a whitening matrix by calculating covariance from output signals from the centering process, and by calculating eigen value and eigen matrix of the covariance;

in a W matrix calculating step, calculating a demixing matrix W by generating a new vector V using the whitening matrix and the output signals from the centering process, by generating an arbitrary 2x2 matrix W, and by applying the V and W to a non-linear function $w^+$, where $w^+=w-E\{vg(w^Tv)\}-E\{g'(w^Tv)\}w$, where g is a Gaussian function;

in a A matrix calculating step, calculating a mixing matrix A by calculating an inverse matrix of output signals from the W matrix calculating step; and in a data restoring step, restoring data using output signals from the A matrix calculating step and output signals from the centering process step.

2. The method as claimed in claim 1, wherein the preprocessing step comprises:

a period measuring step for obtaining a period of the output signals from the A/D conversion step, using autocorrelation;

an interleaving process step for interleaving the output signals from the A/D conversion step, data by relocating the output signals from the A/D conversion step in a predetermined sequence of amplitude according to the period obtained in the period measuring step;

a time low-pass filtering step for transforming, for each sampling point of output signals from the interleaving process step, a current value of the sampling point into an average value of the sampling point, a previous sampling point and a next sampling point; and an innovation process step for subtracting, from a current output value from the time low-pass filtering step, an average value of previous output values from the time low-pass filtering step.

3. The method as claimed in claim 1, wherein the data restoring step comprises:

a step for deciding Photoplethysmography(PPG) signal between separated Photoplethysmography(PPG) signal and noise signal using the demixing matrix W, and then restoring sign and gain of the measured Photoplethysmography(PPG) signal using the mixing matrix A;

a step for calculating a ratio R of normalized transmitted amount of the red and infrared lights from the mixing matrix A; and a step for calculating the arterial oxygen saturation ($SpO_2$), using the ratio R, based on below formula Arterial oxygen saturation $(SpO_2)(\%)=a-bR$, where $107 \leq a \leq 110$, $25 \leq b \leq 32$.

* * * * *